US012759974B2

(12) United States Patent
Dente et al.

(10) Patent No.: US 12,759,974 B2
(45) Date of Patent: Oct. 13, 2026

(54) REACTOR FOR THE SYNTHESIS OF UREA

(71) Applicant: Casale SA, Lugano (CH)

(72) Inventors: Mario Dente, Milan (IT); Leonardo Marrone, Mercallo (IT); Federico Maffietti, Como (IT)

(73) Assignee: Casale SA, Lugano (CH)

(*) Notice: Subject to any disclaimer, the term of this patent is extended or adjusted under 35 U.S.C. 154(b) by 1124 days.

(21) Appl. No.: 17/624,518

(22) PCT Filed: Jun. 9, 2020

(86) PCT No.: PCT/EP2020/065962

§ 371 (c)(1),
(2) Date: Jan. 3, 2022

(87) PCT Pub. No.: WO2021/001121

PCT Pub. Date: Jan. 7, 2021

(65) Prior Publication Data

US 2022/0395798 A1 Dec. 15, 2022

(30) Foreign Application Priority Data

Jul. 2, 2019 (EP) .................................... 19183879

(51) Int. Cl.
*C07C 273/04* (2006.01)
*B01J 19/00* (2006.01)
(Continued)

(52) U.S. Cl.
CPC ........... *C07C 273/04* (2013.01); *B01J 19/006* (2013.01); *B01J 19/24* (2013.01); *B01J 19/32* (2013.01);
(Continued)

(58) Field of Classification Search
None
See application file for complete search history.

(56) References Cited

U.S. PATENT DOCUMENTS 2,332,243 A * 10/1943 Mccarthy ................ B01D 3/18 261/114.2
4,318,870 A * 3/1982 Haselden ................ B01D 3/22 261/114.1
(Continued)

FOREIGN PATENT DOCUMENTS

EP 0495418 A1 7/1992
WO 96/07474 A1 3/1996
(Continued)

OTHER PUBLICATIONS

International Search Report dated Aug. 18, 2020 issued in connection with PCT/EP2020/065962.
(Continued)

*Primary Examiner* — Jennifer A Leung
(74) *Attorney, Agent, or Firm* — Blank Rome LLP

(57) ABSTRACT

A reactor for the synthesis of urea comprising a vertical shell and perforated baffles or trays (3) arranged to define compartments of the reactor, wherein each baffle comprises an array of individual perforated tiles (10) wherein each tile (101) comprises side walls (101A-101D) and a top face (101F), the side walls having first perforations for the liquid and said top face having second perforations for the gas, wherein said second perforations are smaller than said first perforations, and the tiles are distributed over the baffle with a two-dimensional pattern where adjacent tiles are separated by gaps (17).

20 Claims, 9 Drawing Sheets

(51) Int. Cl.
*B01J 19/24* (2006.01)
*B01J 19/32* (2006.01)

(52) U.S. Cl.
CPC ................. *B01J 2219/00024* (2013.01); *B01J 2219/00164* (2013.01); *B01J 2219/00777* (2013.01); *B01J 2219/185* (2013.01); *B01J 2219/32231* (2013.01); *B01J 2219/32244* (2013.01); *B01J 2219/32248* (2013.01); *B01J 2219/32275* (2013.01); *B01J 2219/3313* (2013.01); *B01J 2219/3322* (2013.01)

(56) References Cited

U.S. PATENT DOCUMENTS

| | | | | |
|---|---|---|---|---|
| 6,131,891 | A | 10/2000 | Resetarits et al. | |
| 2003/0019737 | A1* | 1/2003 | Matsumoto .............. | B01D 3/22 203/99 |

FOREIGN PATENT DOCUMENTS

| | | | |
|---|---|---|---|
| WO | 97/15388 | A1 | 5/1997 |
| WO | 99/46037 | A1 | 9/1999 |
| WO | 2013/008147 | A2 | 1/2013 |

OTHER PUBLICATIONS

Written Opinion of the International Searching Authority dated Aug. 18, 2020 issued in connection with PCT/EP2020/065962.
International Preliminary Report on Patentability dated Nov. 9, 2021 issued in connection with PCT/EP2020/065962.
Ullmann's Encyclopedia of Industrial Chemistry, Wiley-VCH Verlag.

* cited by examiner

FIG. 4
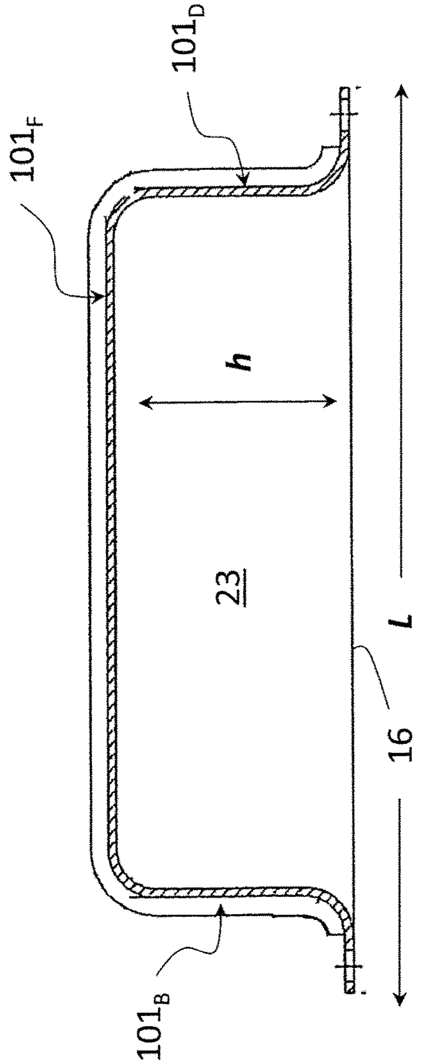
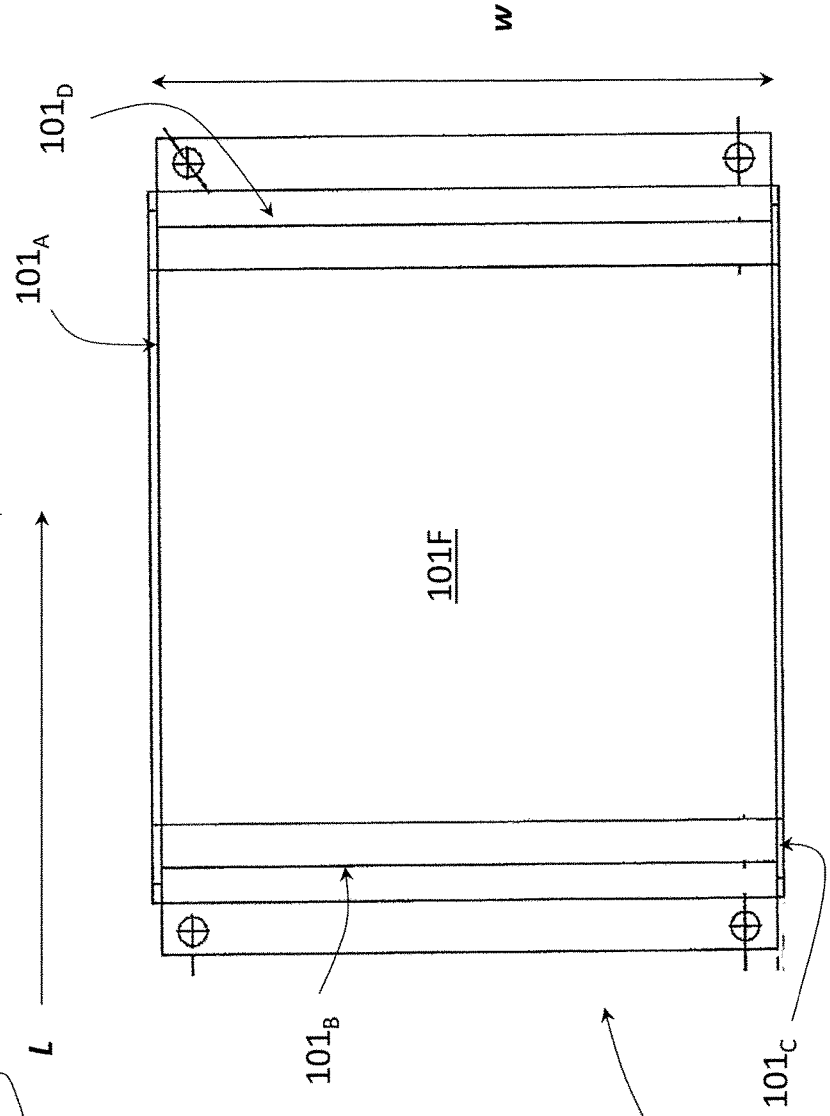
FIG. 3

FIG. 11
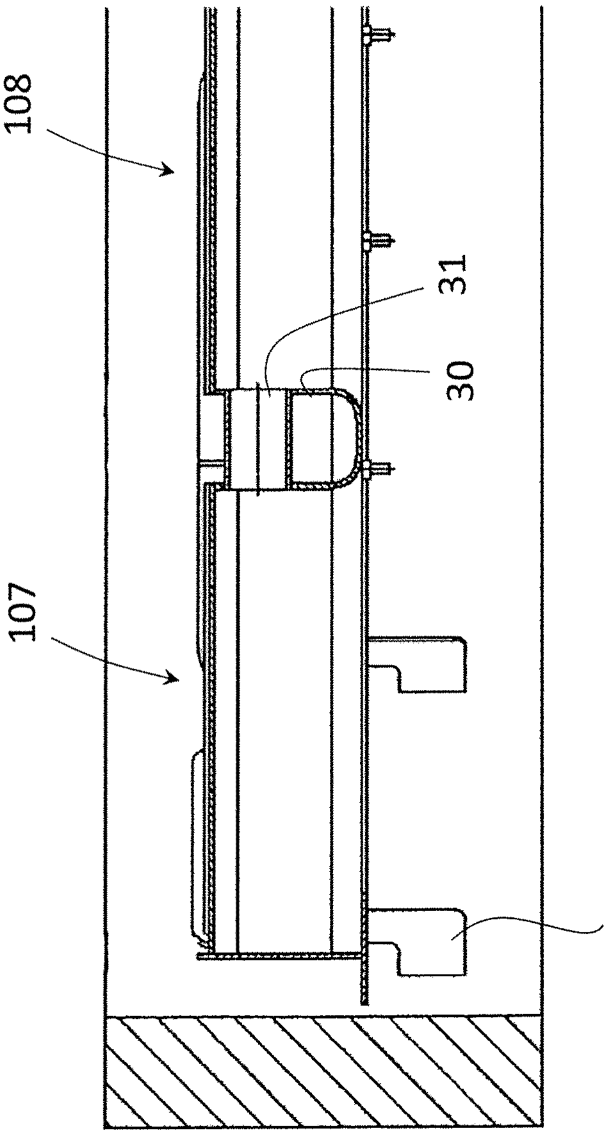
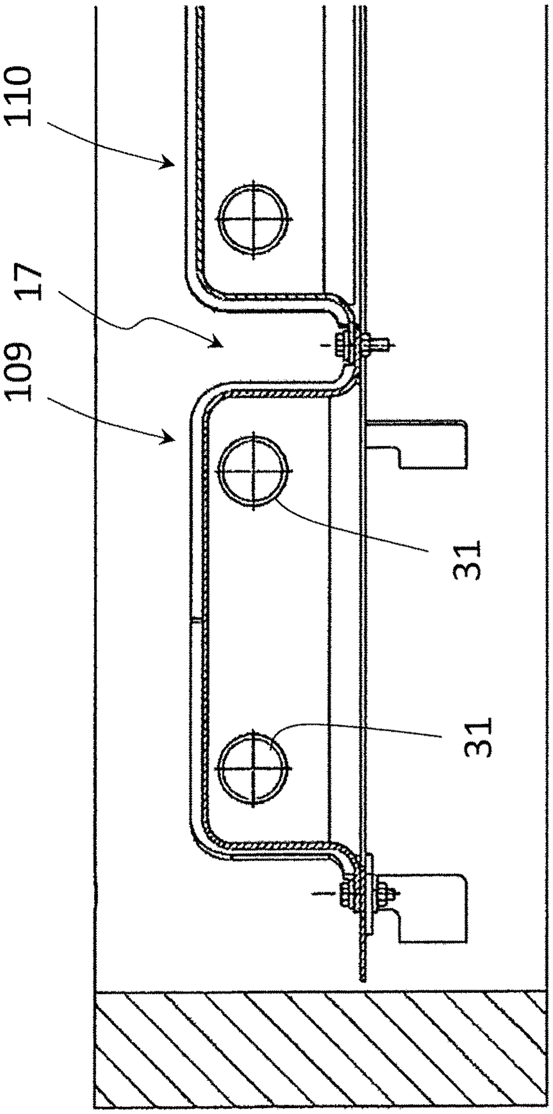
FIG. 12

REACTOR FOR THE SYNTHESIS OF UREA

CROSS-REFERENCE TO RELATED APPLICATIONS

This application is a national phase of PCT/EP2020/065962, filed Jun. 9, 2020, and claims priority to EP 19183879.6, filed Jul. 2, 2019, the entire contents of both of which are hereby incorporated by reference.

FIELD OF THE INVENTION

The invention relates to a reactor for the synthesis of urea.

PRIOR ART

Urea is industrially produced by reacting ammonia and carbon dioxide. A discussion of the various processes and related plants for the urea production can be found in literature, e.g. Ullmann's Encyclopaedia of Industrial Chemistry, Wiley-VCH Verlag.

The urea-forming reaction takes place in a reactor under a high pressure and high temperature. All urea reactors are known to have a relatively low efficiency of conversion, which means that the reactor effluent contains a significant amount of unconverted matter, mostly in the form of unconverted ammonium carbamate. Various equipment downstream the reactor are provided to separate and recover the unconverted matter, which are however expensive and may represent a bottleneck in terms of capacity. There is therefore a strong incentive to improve the yield of conversion in the reactor.

In a urea reactor, a liquid phase and a vapor phase coexist. The urea reactor is therefore a complex two-phase system which is still the subject of study and investigation. It is known however that the kinetics system of a urea reactor can be described with a good accuracy by the following three chemical reactions, wherein the index liq denotes the liquid state:

$$CO_2, liq + 2\ NH_3, liq \longrightarrow NH4^+ + NH_2CO2^- \quad (1)$$

$$H_2O\ liq + NH_2CO_2^- \longrightarrow NH_3, liq + HCO_3^- \quad (2)$$

$$NH_4^+ + NH_2CO_2^- \longrightarrow urea + H_2O\ liq \quad (3)$$

Reaction (1) is exothermic and fast. Reaction (2) is endothermic and fast. Reaction (3) is endothermic and slow. The reaction (3) involves the formation of urea from dehydration of ammonium carbamate.

Reactions (1), (2) and (3) take place in the liquid phase. A significant amount of the $CO_2$ and ammonia, however, are normally fed to the reactor in the gaseous phase and need to condensate to form ammonium carbamate and to further hydrolyze to urea. Therefore, a vapor and a liquid phase coexist within the reactor. This liquid-vapour equilibrium can be approximately described by the following additional equations where (g) denotes gas and (l) denotes liquid:

$$CO_2(g) \longleftrightarrow CO_2(l)$$

-continued $$NH_3(g) \longleftrightarrow NH_3(l)$$

The heat and mass transfer between the liquid phase and the vapor phase is crucial for the overall conversion of reactants to urea.

In a common embodiment, the urea reactor is a vertical item wherein the reagents are introduced in the lower part and the urea-containing liquid effluent is collected from the upper part, usually via a downcomer pipe. An upward flowing mixture of gas and liquid is established inside this kind of vertical reactor. It is known the ideal behavior of such reactor is a plug-flow regime wherein urea forms progressively from bottom to top, and various efforts have been made to provide internals of the reactor specifically designed to approximate the plug-flow model, to increase the heat and mass transfer between the phases and ultimately the urea conversion yield. The heat and mass transfer is the rate determining step of the overall reaction.

To the above purpose, it is known the benefit of dividing the internal volume of the reactor into several compartments separated by suitable perforated baffles or trays.

EP 495 418 discloses perforated baffles with first surfaces having large perforations for the liquid and second surfaces having small perforations for the vapor phase, said surfaces being arranged to provide separate adjacent concurrent paths for the liquid phase and the vapor phase. In the region above the baffles, this design creates emulsion regions above the second surfaces (gas perforated area) and clean liquid regions between adjacent emulsion regions. Particularly, it discloses the perforated baffles formed by elongated parallel elements with a trapezoidal cross section.

Over the years, the trays described in EP 495 418 have performed very efficiently. However there is a continuous effort to improve the internals of urea reactors. The urea reactor is an expensive item, mainly because it operates at a high pressure and temperature and in a very aggressive environment, therefore requiring expensive materials. A gain in the reactor yield means a smaller and less expensive reactor for a given production of urea or, similarly, the ability to produce more urea for a given size and residence time of the reactor.

SUMMARY OF THE INVENTION

The aim of the invention is to improve the yield of conversion of the current state of the art urea reactors. Particularly, one aim of the invention is to improve the heat and mass transport phenomena between the gas phase (vapor phase) and liquid phase.

The aims is reached with a reactor for the synthesis of urea comprising a vertical shell and at least one internal perforated baffle arranged to define compartments of the reactor, characterized in that said baffle comprises an array of individual perforated tiles wherein each tile comprises side walls and a top face, at least one of the side walls having first perforations and said top face having second perforations, wherein said second perforations are smaller than said first perforations, and the tiles are distributed over the baffle with a two-dimensional pattern and adjacent tiles are separated by gaps.

Each tile is substantially a prismatic structure projected upwards, with side walls and a top face. It can also be regarded as a box with a full bottom aperture to collect the rising mixture, and perforated faces with apertures (e.g. holes) specifically designed for the liquid or for the gas.

The tiles are distributed over the surface area of the baffle. Said surface area of the baffle denotes an area in a horizontal plane perpendicular to the axis of the reactor. This can also be termed a cross sectional area of the baffle and may substantially correspond to the cross sectional area of the reactor because the baffle has a diameter close to the internal diameter of the reactor. This cross sectional area has generally the shape of a disc.

Being distributed over the surface area of the baffle with a two-dimensional pattern, the tiles of the baffle collectively form a two-dimensional tiling of the disc-shaped surface area.

The tiles provide an alternation of highs and lows over the surface of the baffle, wherein highs correspond to the top faces of the tiles, and lows correspond to the gaps between tiles. Due to the two-dimensional patterns, the highs and lows alternate according to perpendicular directions, for example in first directions and second directions which are perpendicular and belong to a horizontal plane.

The second perforations are smaller than the first perforations, so that the first perforations provide a preferential route for the liquid phase and the second perforations provide a preferential route for the vapor phase (gaseous phase). Accordingly, when the upward flowing mixture encounter a baffle, the liquid phase flows predominantly through the side walls of its tiles and the vapor phase flows predominantly through the top faces.

As a consequence of this, each tile performs a phase separation and each individual tile generates emulsion regions and clean liquid regions above the baffle. The term clean liquid denotes a deareated liquid.

Preferably a baffle has no liquid or gas passage other than the first and second perforations of the tiles, apart from a peripheral gap between the baffle and the internal lining of the pressure vessel. Therefore, the rising mixture is distributed between the tiles and the mixture captured by one tile can only pass through the first and the second perforations. As stated above, due to the different size of the perforations, the liquid will flow predominantly through the side walls of the tile, while the vapor phase will emerge predominantly from the top face.

The array of tiles may include rows and columns according to perpendicular directions, each row and each column including at least two tiles. For example the array include rows of tiles aligned in a first direction and columns of tiles aligned in a second direction, the first direction being perpendicular to the second direction, the first and second direction belonging to a plane perpendicular to the axis of the reactor (horizontal plane).

Preferably the array of tiles is symmetrical with respect to at least one vertical plane (plane parallel to the axis of the reactor); more preferably with respect to two orthogonal vertical planes.

In a preferred embodiment, the tiles are arranged with a square pitch or a rectangular pitch to form a matrix-like (chessboard) array of tiles. In a different embodiment the rows or the columns of tiles may be staggered, inclined or differently arranged. For example the tiles may be arranged with a triangular pitch. The terms of square pitch or rectangular pitch or triangular pitch denote that centre points of the top faces of adjacent tiles are arranged at the vertices of squares, rectangles or triangles respectively.

Preferably, the side walls of the tiles are vertical walls and the top face has a horizontal surface. Preferably the vertical walls and/or the top face are planar. In some embodiments however the side walls of some or all tiles may be inclined relative to the vertical direction and/or the top face of some or all tiles may be inclined relative to the horizontal direction.

In a preferred embodiment, each tile has a length/width aspect ratio of 0.5 to 1.5. Said aspect ratio is a ratio of a maximum length over a maximum width of the tile, wherein the length and the width are taken according to perpendicular directions in a horizontal plane.

Some features of the baffle can be described in relation to a reference base plane. The reference base plane gives the elevation in the reactor where the baffle is installed. For example a reference base plane may correspond to the upper face of a supporting ring of the baffle.

The individual tiles project upward relative to said reference base plane. All tiles of each baffle have preferably the same height from the base plane of the baffle. Said height is the distance of the top surface from the base plane in the direction of the axis of the reactor (vertical direction).

Each tile is separated from adjacent tiles by gaps. Preferably the gaps extend in directions parallel to the side walls of the tile. Each tile, accordingly, forms an individual box-like structure.

The total area of the first perforations of each baffle (perforated area) is preferably 2% to 3% of the internal cross section of the pressure vessel. The total area of the second perforations preferably ranges from 0.4% to 1.5% of said internal cross section of the pressure vessel. Said area of the second perforation depends on the vapor fraction of the mixture and preferably decreases from bottom to top of the reactor. For example the lower baffles may have a greater number of second perforations than the upper baffles.

The first perforations are substantially larger than the second perforations. Within a baffle, the first perforations may be 20 to 100 times the second perforations or even more. The individual area of each first perforation is preferably 300 to 600 $mm^2$, more preferably 350 to 550 $mm^2$. The individual area of each second perforation is preferably about 3 to 15 $mm^2$.

The first perforations and/or the second perforations may be circular holes or elongate slots. The first perforations are arranged such as to form a horizontal array of spaced holes on some or all the side walls. The second perforations may be arranged according to a specific pattern, for example with a square or triangular pattern.

The first perforations may be arranged on only some or all of the side walls, for a given total surface area of the passages. Preferably all side walls are perforated.

The second perforations, in a preferred embodiment, are circular holes with a diameter not greater than 4 mm, preferably of 2 mm to 3 mm, more preferably 2 mm. This reduces a resistance against heat and mass transfer, as will be explained below.

The number of tiles per baffle may differ. As a general rule, a greater number is preferred to separate the phases; a smaller number may however be preferred for a simple construction. In practical embodiments, the number of tiles per baffle preferably ranges from 12 to 30, more preferably 18 to 26.

The size and/or shape of the tile may differ according to the position of the tiles in the pattern. For example, a baffle may include first tiles with a square shape delimited by four side walls arranged relative to each other at right angles, and second tiles with a polygonal shape having at least one side wall inclined relative to the adjacent side walls. Said second tiles may be positioned peripherally in order to approximate the disc shape of the cross-sectional area of the reactor.

A baffle is preferably fixed to the pressure shell via a supporting ring for fixation to the pressure shell of the reactor. An upper planar ring surface of said supporting ring may coincide with (i.e. belongs to) a reference base plane of the baffle.

A baffle may include supporting beams with opposite ends connected to the supporting ring. The tiles may be secured (e.g. bolted) to said supporting beams.

Each tile may be formed by metal sheets according to preferred embodiments. Each metal sheet may form one or more of the side walls and the top face. The metal sheets which compose a tile are preferably joined in a gastight or substantially gastight manner, so that the liquid or gas passage is only allowed through the perforations.

In a preferred embodiment, a baffle may include a folded metal sheet which define the top face and two opposite side walls of the tiles, for example a front wall and a rear wall. The baffle may then include additional metal sheets to form the lateral walls.

In another embodiment, the baffle may include self-supporting structures wherein each of said structures form a plurality of tiles aligned in a row from one end to the opposite end of the baffle, and the structures are arranged parallel to form the two-dimensional array. Said structures may be directly connected to the supporting ring of the baffle.

The number of baffles in the reactor may vary. Preferably a vertical urea reactor according to the invention comprises a set of 8 to 20 of the above described baffles. Within a set of baffles in a reactor, the baffles may have the same pattern of tiles or different patterns.

An aspect of the present invention is also a process for the synthesis of urea according to the claims.

The process includes the formation of a mixture of the liquid phase and gas phase flowing upwards in a vertical urea reactor and withdrawing a liquid effluent from an upper region of the reactor, and includes passing the mixture though a plurality of baffles aligned vertically in the reactor, wherein each baffle comprises a two-dimensional pattern of individual tiles separated by gaps, each tile comprises side walls wherein at least one side wall has first perforations for the liquid phase, and a top face with second perforations for the gaseous phase, wherein the second perforations are smaller than the first perforations, so that the liquid phase of the mixture flows predominantly through the first perforations and the gaseous phase flows predominantly through the second perforations, and each tile performs a separation of the gas phase from the liquid phase.

Another aspect of the present invention is a method of revamping a urea reactor according to the claims, wherein at least one internal baffle of the urea reactor is replaced with a new baffle including perforated tiles arranged in a two-dimensional pattern, as above described.

The various preferred embodiments of the baffles are also applicable to the synthesis process and to the revamping process.

It should be noted that the term reactor for the synthesis of urea, or urea reactor, denotes a reactor which is able to withstand the typical urea-forming reaction conditions, for example a pressure of more than 80 bar, typically around 150 bar, temperature around 190° C. and the corrosive attack of the ammonium carbamate.

The advantages of the invention are now discussed.

The main advantage of the invention is that the structure of the baffle with perforated tiles arranged in a two-dimensional pattern improves the separation between the vapor phase and the liquid phase, and improves the heat and mass transfer.

Particularly, each individual tile receives a certain fraction of the upward flowing mixture and the mixture captured by a tile is substantially separated into gas and liquid thanks to the preferential side passages for the liquid and for the vapor, provided respectively by the large perforations of the side walls and small perforations of the top face.

Thanks to the two-dimensional pattern arrangement of the tiles, the flow above (i.e. downstream) the baffle is more fragmented into regions of predominant gas and regions of predominant liquid, compared to the prior art.

As a matter of fact, each tile tends to form a downstream pattern of regions of predominant liquid and regions of predominant vapors. It can be said that each tile generates a respective emulsion region above the top face surrounded one or more clean liquid regions generated by the liquid passed through the perforated side walls. Compared to the prior art, a greater number of such regions is created and large zones of liquid only or gas only are avoided.

Particularly, the inventors have found that, in a urea reactor wherein separation baffles form an emulsion region and a clean liquid region, as a result of different preferential passages for the liquid phase and the gas phase, the key factor which negatively affects the heat and mass transfer rate is the resistance between the emulsion and the clean liquid region. The invention substantially reduces this factor introducing additional boundary surfaces between the emulsion region and the clean liquid region.

A second factor against heat and mass transfer is the resistance between each bubble and the surrounding liquid within the emulsion. This factor has normally a less impact than the above described resistance between the emulsion and the clean liquid region; however it may become relevant due to the reduction of said resistance achieved by the present invention. This second factor can be reduced by appropriate small gas holes, preferably having a diameter not greater than 3 mm, as above mentioned.

DESCRIPTION OF FIGURES

FIG. 3 is a top view of one tile of the baffle of FIG. 2.

FIG. 4 is a sectional view of the tile of FIG. 3.

FIGS. 11 and 12 are sectional views according to planes XI and XII of FIG. 10.

DETAILED DESCRIPTION

Figure 1:
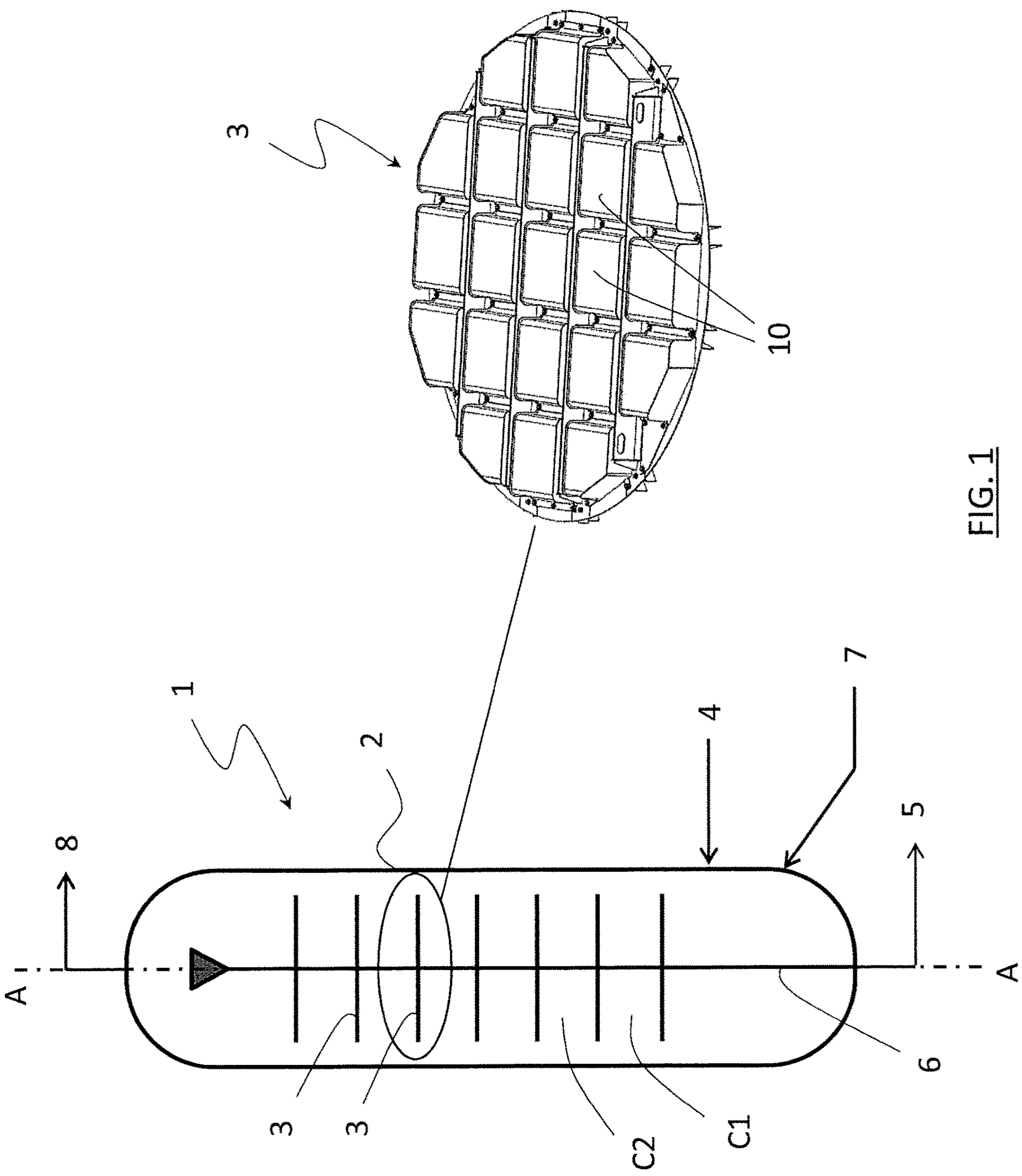
FIG. 1 is a scheme of a urea reactor including a plurality of internal baffles, including a detail of one of the baffles.

FIG. 1 illustrates a reactor 1 for the synthesis of urea comprising a shell 2 with a vertical axis A-A and perforated baffles (or trays) 3 arranged inside the shell 2 to define several compartments of the reactor C1, C2, . . . Cn.

The reactor receives the reagents in its lower part, for example from a feed line 4, and has an output line 5 connected to a downcomer pipe 6 for a urea-containing liquid effluent collected from the top compartment above the uppermost baffle.

The reactor 1 may be part of a high-pressure loop including a stripper, a condenser and possibly a scrubber; the feed line 4 may carry the condensate from the high-pressure condenser together with fresh gaseous ammonia and possibly gaseous carbon dioxide. A separate feed line 7 of gaseous carbon dioxide may also be provided if necessary.

The effluent line 5 may feed the reactor effluent to a stripper. A reactor overhead gas is withdrawn from top of the reactor via a line 8 and may be sent to a scrubber.

The above details of the reactor 1 are known to a skilled person and may differ according to the urea synthesis process which is implemented, for example self-stripping, ammonia stripping or CO2 stripping. Therefore the reactor 1 is not further described.

One of the baffles 3 is illustrated in the enlarged detail of FIG. 1 and is now described with reference to FIGS. 2 to 9.

Figure 2:
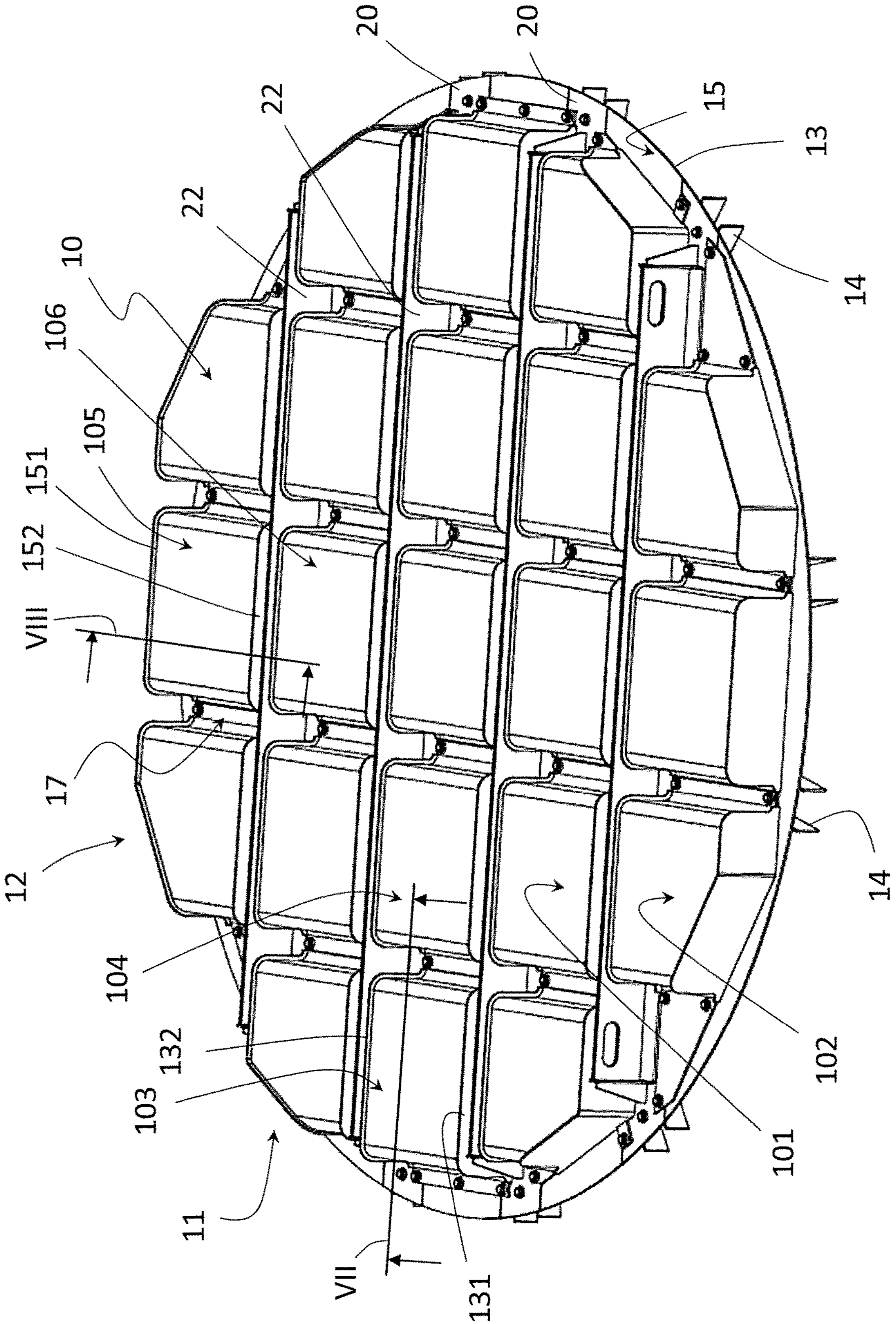
FIG. 2 is a view of one baffle of the reactor of FIG. 1, according to a first embodiment.

The baffle 3 includes a plurality of box-shaped tiles generally denoted in FIG. 1 with the reference 10. The tiles 10 form a two-dimensional pattern. In the present example, as best seen in FIG. 2, the tiles 10 are arranged with a square pitch and form a matrix pattern of rows 11 and columns 12, particularly five rows and five columns in the shown example. Each tile 10 is separated from adjacent tiles by gaps 17.

The tiles 10 are supported by a ring 13 which in turn is anchored to the inside surface of the shell 2 by a plurality of supports 14. A planar upper surface 15 of the ring 13 defines a plane 16 (FIGS. 4 and 6) perpendicular to the axis A-A which can be regarded as a reference base plane of the baffle 3. This plane 16 denotes a base elevation of the baffle 3 within the reactor 1.

Each tile 10 is basically a prismatic body projecting upward from the ring 13 (therefore upward from the base plane 16) and comprising side walls and a top face.

FIG. 2 indicates exemplary tiles 101 to 106 which are described below.

FIG. 3 illustrates a first tile 101 having side walls 101A to 101D and a top face 101F. Some or all of the side walls 101A to 101D have perforations with a size adapted to provide a preferential route for the liquid phase. The top face 101F has smaller perforations adapted to provide a preferential route for the gaseous passage. The perforations are not shown.

The side walls 101A to 101D are arranged at right angles, which means each side wall forms a square angle with the adjacent side walls.

The top face 101F is located at a vertical distance h from the base plane 16 according to the direction of the axis A-A. Said distance h can be termed the height of the tile 101 relative to the base plane 11. Preferably all tiles of the baffle 3 have the same height.

The tile 101 has also a length L and a width w. Preferably said length and width are equal or slightly different; for example the ratio L/w is preferably in the range 0.5 to 1.5, and more preferably 0.8 to 1.2. Preferably said ratio is 1 or close to 1, so that the top face 101F, seen from the above, is a square or is close to a square.

It can be noted that different tiles 10, within a baffle 3, may have different length and/or different width.

Figure 5:
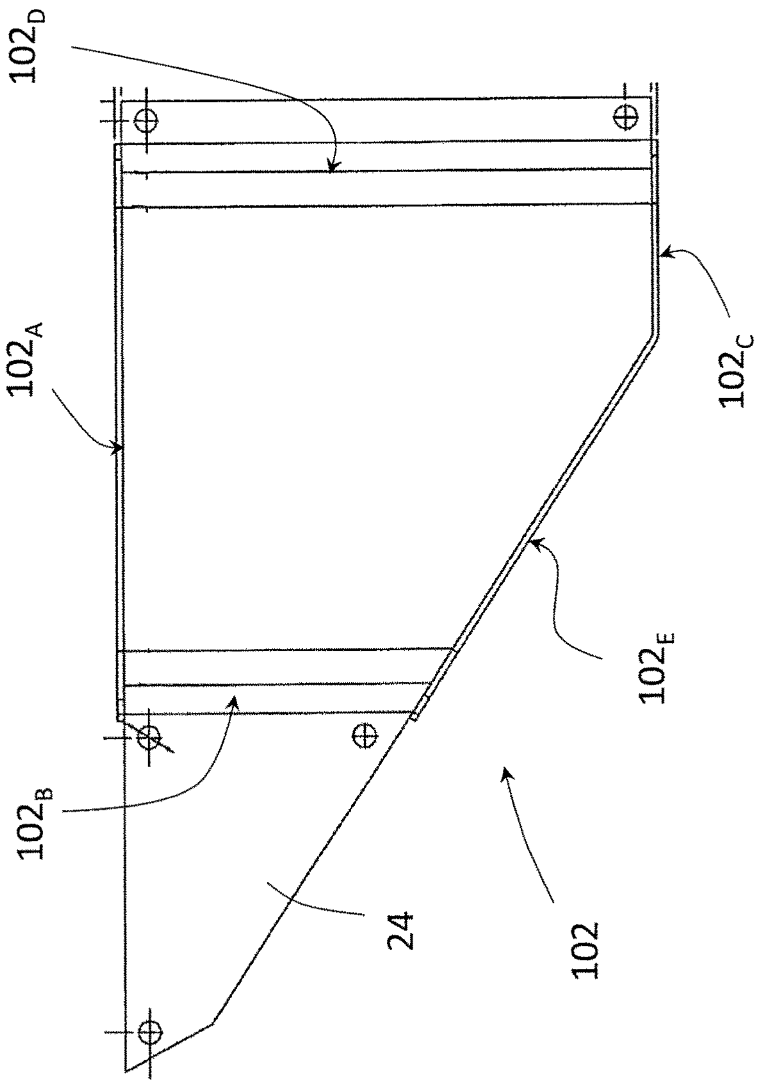
FIG. 5 is a top view of another tile of the baffle of FIG. 2.
Figure 6:
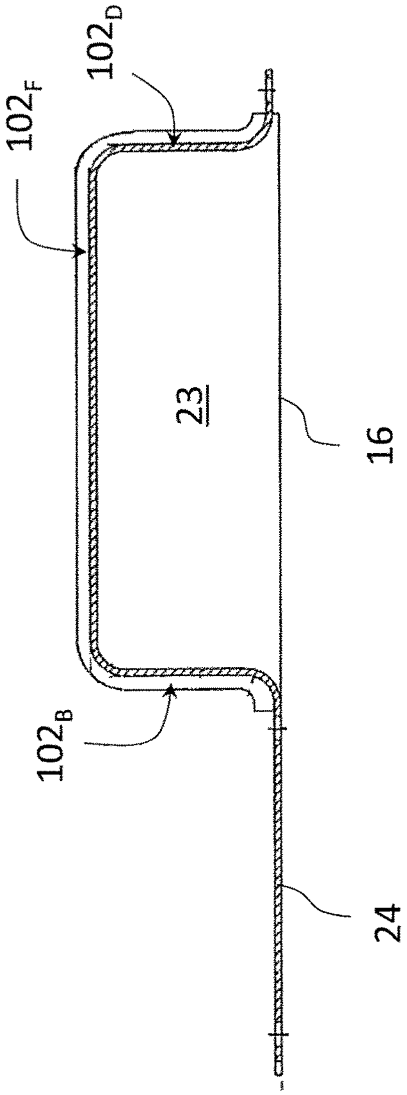
FIG. 6 is a sectional view of the tile of FIG. 5.

FIGS. 5 and 6 illustrate a second tile 102 which has four side walls 102A to 102D and a top face 102F and, additionally, an inclined side wall 102E to join short side walls 102B and 102C. This shape with an inclined side wall may better conform to an arc of the circular cross section. The tile 102 has also a plate 24 for fixation to the ring 13.

Tiles with inclined side walls, such as the tile 102, are preferably provided at the periphery of the baffle 3, as illustrated in FIG. 2.

The side walls of each tile 10 are preferably vertical and parallel to the axis A-A and the top face is preferably plane and perpendicular to the same axis.

It can be appreciated that the two-dimensional pattern of the tiles 10 created an alternation of highs and lows over the upper surface of the baffle 3. The highs correspond to the top faces of the tiles, e.g. the top faces 101F and 102F. The low (recesses) correspond to the gaps 17. The highs and lows may also be regarded as projections and recesses relative to a median plane of the baffle (e.g. a plane parallel to the plane 16 passing at half the height h).

The baffle 3 has an upper face and a lower face. Each tile 10 defines a chamber on the lower face of the baffle 3 and said chamber, in operation, will receive a fraction of the upwardly flowing mixture of gas and liquid.

For example the tile 101 defines a chamber 23 (FIG. 4). It can be understood that the fraction of the mixture collected in the chamber 23 will flow through the perforations of its side walls and top face and, particularly, the liquid phase will flow mostly through the larger first perforations whilst the gas (vapor) phase will flow mostly through the smaller second perforations. This is due to the different size and location of the first and second perforations. Similarly, FIG. 6 shows the chamber 23 defined by the tile 102.

A tile 10 may comprise a metal sheet which is shaped and possibly cut to form the top face and two opposite side walls, and may comprise two or more additional metal sheets arranged to form the other side walls.

Figure 7:
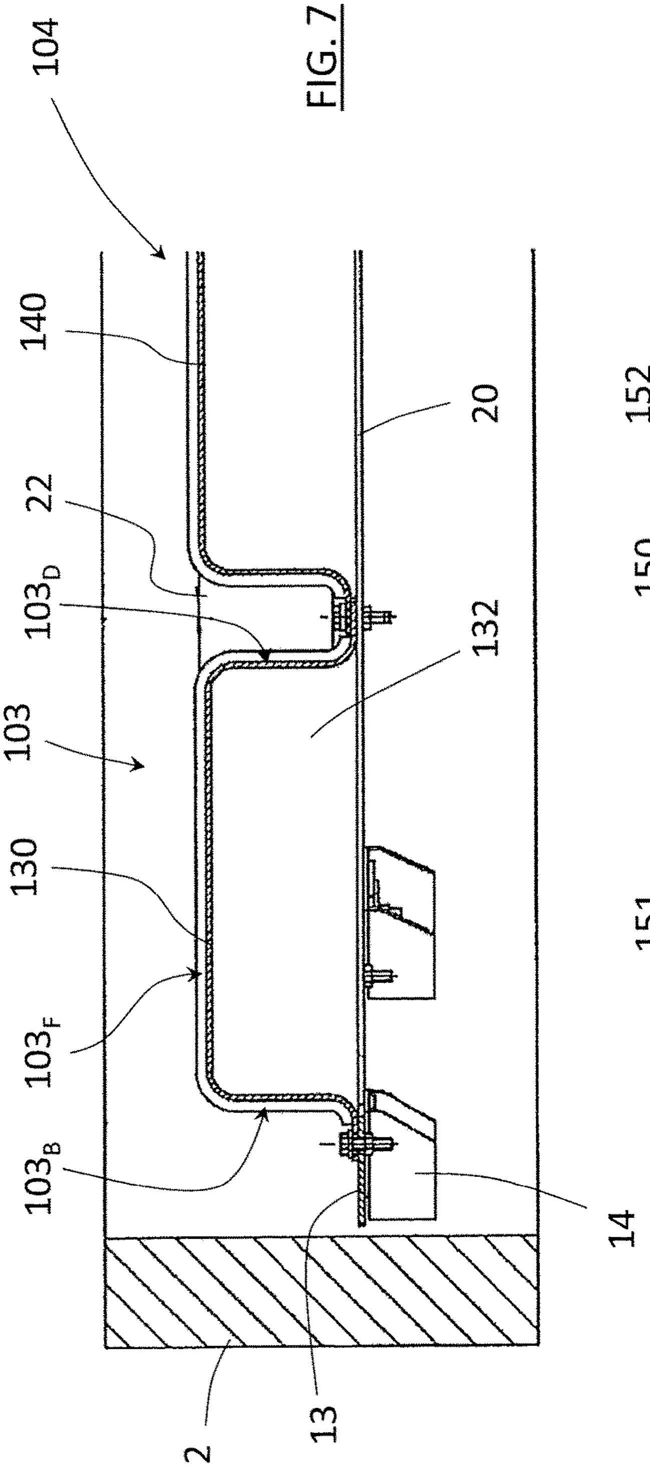
FIG. 7 is a sectional view according to plane VII of FIG. 2.

The sectional view of FIG. 7 illustrates exemplary tiles 103 and 104 connected to supporting beams 20. The supporting beams 20, in this embodiment, extends from one side to the other side of the baffle 3 and provide an intermediate support for the tiles 10 as well as increased resistance to bending.

The tile 103 comprises a metal sheet 130 shaped to form two side walls, e.g. a front side wall 103B and a rear side wall 103D, and the top face 103F. The ends of the metal sheet 130 are fixed (e.g. bolted) to the ring 13 or to the supporting beams 20 (see also FIG. 9). The tile 103 further includes two metal sheets 131, 132 forming the left and right side walls.

The tile 104 next to tile 103 is similar, including a metal sheet 140 to form a front wall and a rear wall and the top face and two metal sheets to form the right and left walls.

Figure 8:
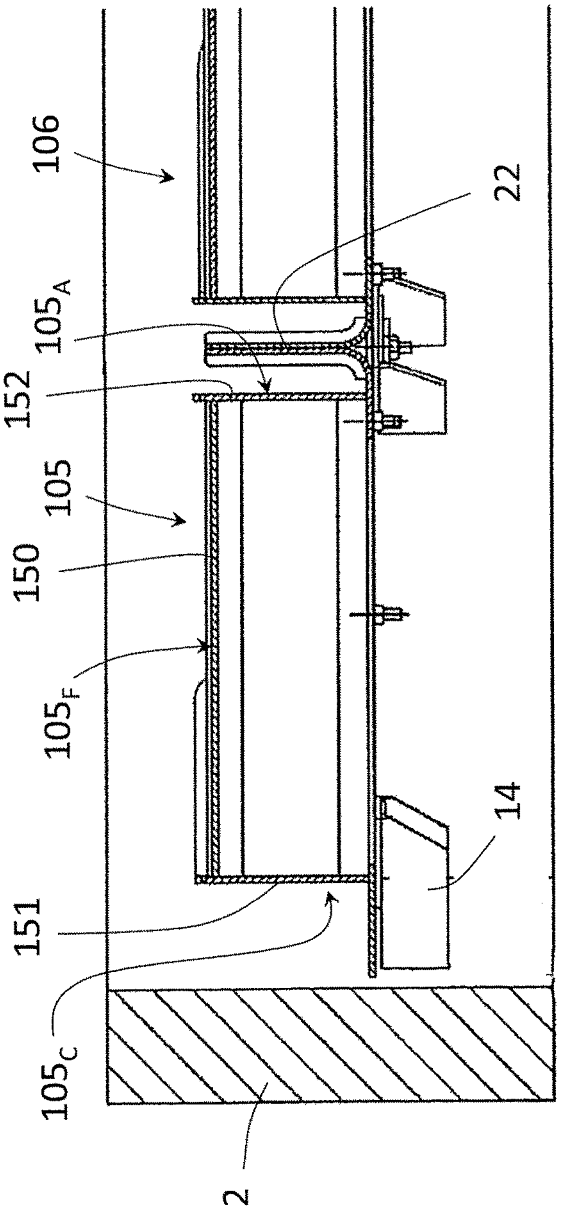
FIG. 8 is a sectional view according to plane VIII of FIG. 2.

FIG. 8 shows a section of another exemplary tile 150, showing a metal sheet 150 forming the top face 105F and the front/rear side walls, and lateral metal sheets 151, 152 forming the left/right side walls 105A and 105C.

FIGS. 7 and 8 also illustrate a plate 22 arranged in the middle of the beam 20 to increase resistance to bending.

Figure 9:
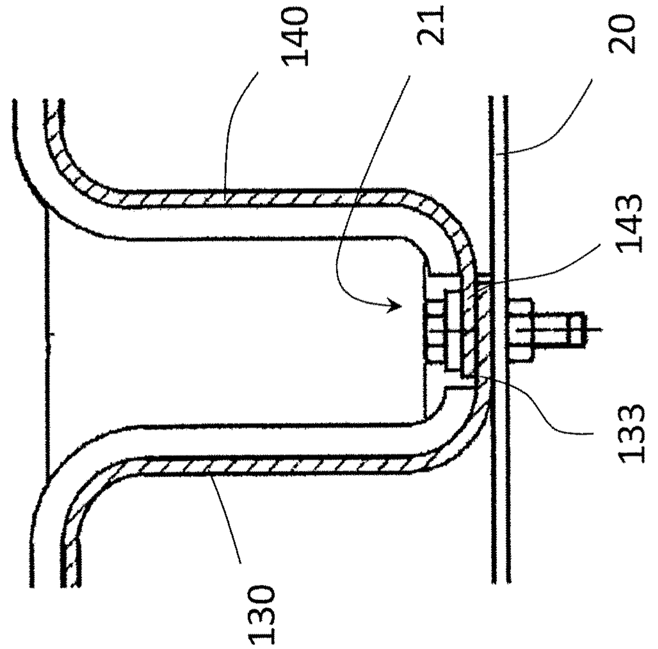
FIG. 9 is a detail of FIG. 7.

FIG. 9 shows a detail of ends 133 and 143 of the metal sheets 130, 140 connected to the beam 20 with a common anchor point such as bolt 21.

Some details of FIGS. 7 to 9 are also indicated in FIG. 2 for easier understanding. In FIG. 7 and FIG. 9, the shell 2 is also illustrated in a cross section.

In tiles with an inclined side wall (e.g. as in FIG. 5), the inclined side wall may be formed by a separate metal sheet or by bending a lateral metal sheet in an appropriate way.

The metal sheets forming one tile are preferably joined in a sealed manner, for example welded. Accordingly, escape of the liquid or gas at the junction of metal sheets is avoided.

Figure 10:
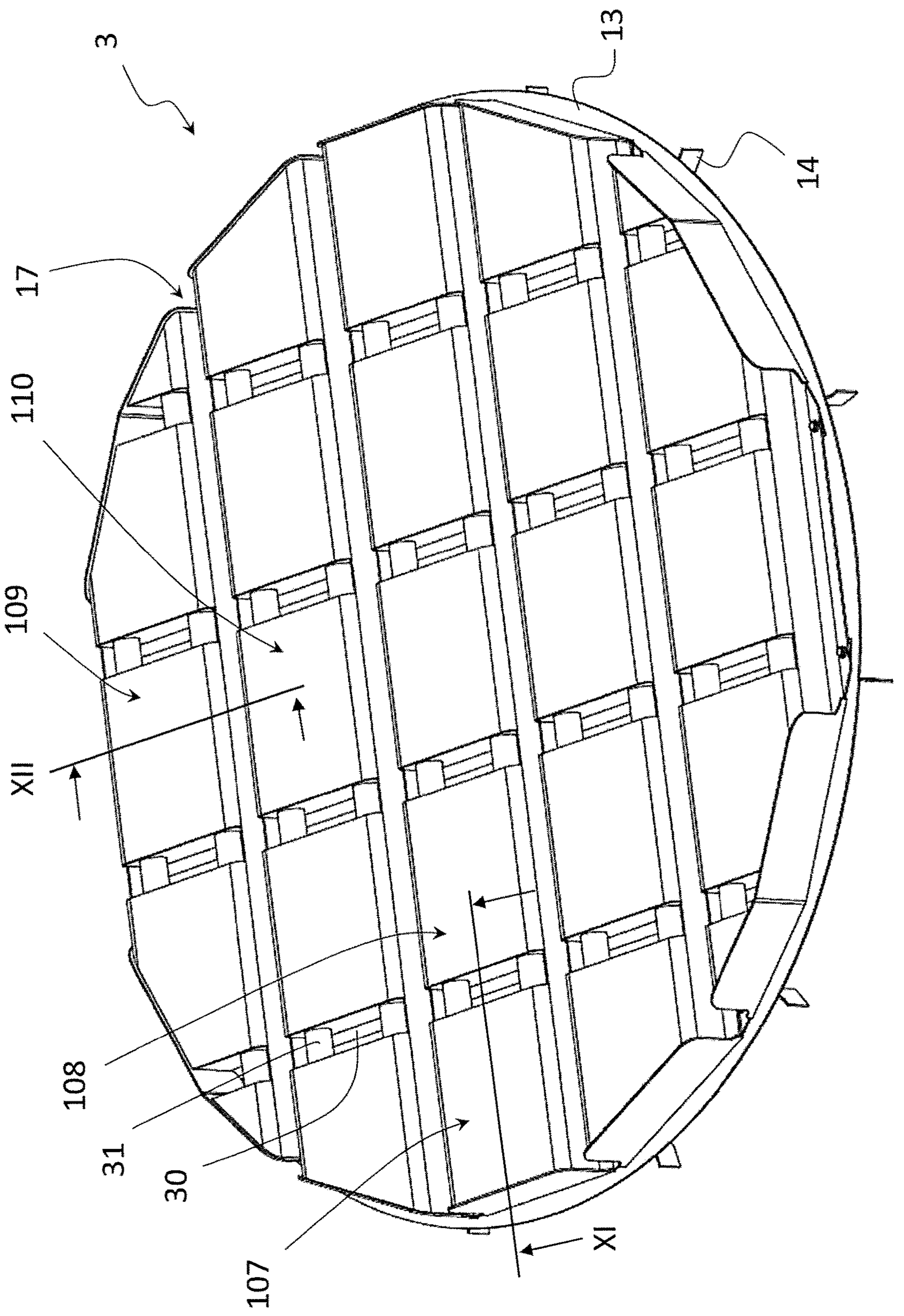
FIG. 10 is a view of one baffle according to a second embodiment.

FIG. 10 illustrates a baffle 3 according to a second embodiment. In this second embodiments the tiles are formed by a folded metal sheet and lateral metal sheet as previously described. However, the tiles in a row are connected together forming a self-supporting structure which is connected at opposite ends to the ring 13, with no need of the supporting beams 20.

This second embodiment includes integrated stiffening beams 30 between adjacent tiles, such as tiles 107, 108 of FIG. 11. Also, gas equalization ducts 31 are preferably provided between adjacent tiles. FIG. 12 illustrates another pair of tiles 109, 110 and a preferred arrangement of two gas equalization ducts 31.

Figure 13:
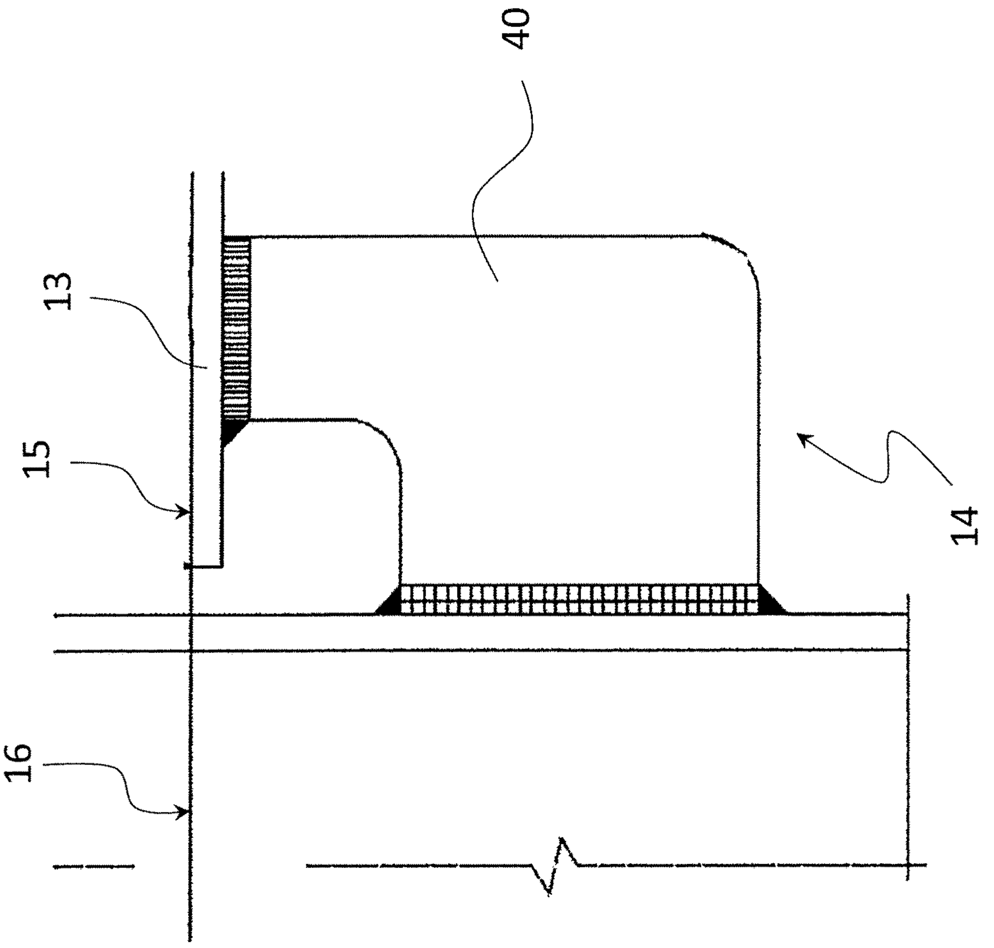
FIG. 13 is a detail of a support of the baffle of FIG. 10.

FIG. 13 illustrates a detail, according to a preferred execution, of a support 14, including a L-shaped plate 40 welded to the shell 2 and to the ring 13. FIG. 13 also illustrates the top face 15 of the ring 13, which coincides with the reference base plane 16. The embodiment of FIG. 13 can be used, preferably but not exclusively, with the second embodiment of FIG. 10.

Comparative Example

The performance of a reactor according to the invention was compared with the performance of a reactor according to the prior art of EP 495 418, with a proprietary mathematical model.

The following assumptions were made for the prior art comparative case: self-stripping process; residence time in the reactor 20 min; production 2216 metric tons per day (MTD); inlet nitrogen to carbon N/C ratio of 3.27; inlet hydrogen to carbon H/C ratio of 0.59; inlet temperature of 140° C.; outlet temperature 193° C. The CO2 conversion was 54.3% overall and 61.9% on liquid basis.

With the same residence time, inlet N/C ratio, inlet H/C ratio and inlet temperature, an overall CO2 conversion of 55.4% and 62.9% on liquid basis was obtained for the reactor according to the invention with a production rate of 2263 MTD.

Therefore the invention gives an advantage in terms of conversion around 1%. The advantage may be greater in case e.g. of a revamping when starting from a less optimized condition.

With a CO2 stripping process, residence time of 30 min, inlet N/C of 3.19, inlet H/C of 0.61, inlet liquid temperature of 174° C., the CO2 conversion was 54.2% overall and 59.1% liquid basis with the prior art, and was increased to 56.3% and 60.6% respectively with the invention. The calculated production rate increased from 2134 MTD to 2217 MTD.

What is claimed is:

1. A reactor for the synthesis of urea comprising a vertical shell and at least one internal perforated baffle arranged to define compartments of the reactor, wherein said at least one internal perforated baffle comprises an array of individual perforated tiles wherein each tile comprises side walls and a top face, at least one of the side walls having first perforations and said top face having second perforations, wherein said second perforations are smaller than said first perforations, and the tiles are distributed over the at least one internal perforated baffle with a two-dimensional pattern and adjacent tiles are separated by gaps wherein the first perforations provide a preferential route for a liquid phase and the second perforations provide a preferential route for a vapor phase in the reactor;

wherein the at least one internal perforated baffle includes self-supporting structures wherein each of said self-supporting structures includes a plurality of tiles aligned in a row from one end to the opposite end of the at least one internal perforated baffle, and the structures are arranged parallel to each other to form said two-dimensional pattern.

2. The reactor according to claim 1, wherein the array of tiles includes rows of tiles aligned in a first direction and columns of tiles aligned in a second direction, the first direction being perpendicular to the second direction, each row and each column including at least two tiles.

3. The reactor according to claim 1, wherein the tiles are arranged mirror-symmetrically with respect to at least one vertical plane parallel to a reactor axis.

4. The reactor according to claim 2, wherein the tiles are arranged with a square pitch or a rectangular pitch to form a matrix array of tiles, or wherein the tiles of rows of tiles or of the columns of tiles are staggered.

5. The reactor according to claim 1, wherein the side walls of the tiles are vertical walls parallel to a vertical axis of the reactor and the top face is perpendicular to the vertical axis of the reactor.

6. The reactor according to claim 1, wherein each tile has an aspect ratio of 0.5 to 1.5, wherein said aspect ratio is a ratio of a maximum length over a perpendicular maximum width of the tile, wherein said maximum length and maximum width are located in a horizontal plane.

7. The reactor according to claim 1, wherein all tiles of the at least one internal perforated baffle have the same elevation from a reference base plane, said elevation being the vertical distance of the top surface from said base plane.

8. The reactor according to claim 1, wherein each tile is separated from adjacent tiles by said gaps, wherein the gaps extend in directions parallel to the side walls of the tile, so that each tile forms an individual box structure.

9. The reactor according to claim 1, wherein each perforation of the first perforations, which are for the liquid passage, has an area of 300 to 600 $mm^2$ and each perforation of the second perforations, which are for the gas passage, has an area of 3 to 15 $mm^2$.

10. The reactor according to claim 1, wherein the first perforations are arranged on some or all of the side walls.

11. The reactor according to claim 1, wherein the first perforations and/or the second perforations are circular holes.

12. The reactor according to claim 1, wherein the number of tiles of said at least one internal perforated baffle is 12 to 30.

13. The reactor according to claim 1, wherein the second perforations are gas holes of a circular shape and having a diameter not greater than 4 mm.

14. The reactor according to claim 1, wherein the at least one internal perforated baffle fits the shape of a solid circle and includes first tiles with a square shape delimited by four side walls arranged relative to each other at right angles, and second tiles with a polygonal shape having at least one side wall inclined relative to the adjacent side walls, the second tiles being positioned peripherally in the at least one internal perforated baffle in order to approximate said solid circle.

15. The reactor according to claim 1, including a respective supporting ring for fixation of each internal perforated baffle to the vertical shell of the reactor.

16. The reactor according to claim 1, wherein each tile includes a plurality of metal sheets, including a folded metal sheet which define the top face and two opposite side walls, and one or more additional metal sheets which form other side walls of the tile.

17. The reactor according to claim 16, wherein said at least one internal perforated baffle includes supporting beams and at least one of the metal sheets of each tile is secured to said supporting beams.

18. The reactor according to claim 3, wherein the tiles are arranged mirror-symmetrically with respect to two orthogonal vertical planes parallel to the reactor axis.

19. The reactor according to claim 12, wherein the number of tiles of said at least one internal perforated baffle is 18 to 26.

20. The reactor according to claim 15, wherein the vertical shell of the reactor is a pressure shell.

* * * * *